United States Patent
Prien (10) Patent No.: US 8,118,810 B2
(45) Date of Patent: Feb. 21, 2012

(54) TARGETING DEVICE FOR BONE IMPLANT

(75) Inventor: Ole Prien, Kiel (DE)

(73) Assignee: Stryker Trauma GmbH (DE)

( * ) Notice: Subject to any disclaimer, the term of this patent is extended or adjusted under 35 U.S.C. 154(b) by 357 days.

(21) Appl. No.: 11/482,443

(22) Filed: Jul. 7, 2006

(65) Prior Publication Data

US 2007/0173836 A1 Jul. 26, 2007

Related U.S. Application Data

(60) Provisional application No. 60/759,376, filed on Jan. 17, 2006.

(30) Foreign Application Priority Data

Apr. 25, 2006 (EP) .................................. 06008538

(51) Int. Cl.
*A61F 5/00* (2006.01)
(52) U.S. Cl. ......................................................... 606/87
(58) Field of Classification Search .................. 606/280, 606/70–71, 281, 197, 96–98, 86, 87
See application file for complete search history.

(56) References Cited

U.S. PATENT DOCUMENTS

| | | | | |
|---|---|---|---|---|
| 4,945,904 | A * | 8/1990 | Bolton et al. | 606/96 |
| 5,423,826 | A | 6/1995 | Coates et al. | |
| 5,676,666 | A | 10/1997 | Oxland et al. | |
| 5,766,174 | A | 6/1998 | Perry | |
| 6,224,601 | B1 | 5/2001 | Friedl | |
| 6,235,034 | B1 * | 5/2001 | Bray | 606/71 |
| 6,267,763 | B1 | 7/2001 | Castro | |
| 6,989,012 | B2 | 1/2006 | Le Huec et al. | |
| 2002/0147450 | A1 * | 10/2002 | LeHuec et al. | 606/61 |
| 2003/0135213 | A1 | 7/2003 | LeHuec et al. | |
| 2004/0015174 | A1 | 1/2004 | Null et al. | |
| 2004/0033469 | A1 * | 2/2004 | Blacklock | 433/173 |

(Continued)

FOREIGN PATENT DOCUMENTS

DE 10131992 1/2003
WO WO-2005/089660 9/2005

OTHER PUBLICATIONS

"Basic Percutaneous Intrumentation and Aiming Arm for 4.5 mm LCP Condylar Plates", Synthes Technique Guide, pp. 1-27.
"Less Invasive Stabilization System (LISS)", Synthes Technique Guide, Proximal Tibia, pp. 1-32.
"Less Invasive Stabilization System (LISS)", Synthes Technique Guide, Distal Femur, pp. 1-36.

(Continued)

*Primary Examiner* — Thomas C. Barrett
*Assistant Examiner* — Sameh Boles
(74) *Attorney, Agent, or Firm* — Lerner, David, Littenberg, Krumholz & Mentlik, LLP (57) ABSTRACT

A medical implant system has parts for detachably establishing a spatial orientation between a body implant such as a bone plate and an aiming device. A contoured portion of a body implant is designed in such a manner that an adapter device can be detachably fastened to the body implant by means of a mechanic form-fit connection. Preferably the form-fitting elements are grooves and protrusions which tightly engage when clamped together. The adaptor device provides a basis for aiming or targeting a device such that the targeting device may be detachably positioned in a stable spatial position with respect to the body implant. Preferably, the adaptor device comprises a dowel pin, a handling device and a clamping element, which elements allow for a quick and easy assembling and disassembling of the adaptor device in a desired alignment.

18 Claims, 6 Drawing Sheets

U.S. PATENT DOCUMENTS

| | | | |
|---|---|---|---|
| 2004/0034356 A1* | 2/2004 | LeHuec et al. | 606/72 |
| 2004/0204717 A1 | 10/2004 | Fanger et al. | |
| 2005/0015093 A1* | 1/2005 | Suh et al. | 606/96 |
| 2005/0085818 A1 | 4/2005 | Huebner | |
| 2005/0287496 A1* | 12/2005 | Niznick | 433/173 |
| 2006/0155284 A1 | 7/2006 | Doherty et al. | |

OTHER PUBLICATIONS

Stryker, Internal document concerning developments on the field of osteosynthesis.

Stryker, Surgical Technique.

Office Action from U.S. Appl. No. 11/478,791, mailed Feb. 2, 2010.

\* cited by examiner

TARGETING DEVICE FOR BONE IMPLANT

CROSS-REFERENCE TO RELATED APPLICATIONS

This application claims the benefit of the filing date of U.S. Provisional Patent Application No. 60/759,376 filed Jan. 17, 2006 and European Patent Application No. 06008538.8 filed Apr. 25, 2006, the disclosures of which are hereby incorporated herein by reference.

BACKGROUND OF THE INVENTION

This invention relates to a medical system comprising an implant, an adaptor device and method for spatially adjusting a targeting or aiming device relative to the implant.

The present invention relates to the field of surgical instruments. In particular, the present invention relates to a medical system for detachably establishing a spatial orientation between a body implant and an aiming device. More particular, the present invention relates to a medical system and parts of the system, which allow for a precise establishing of a relative spatial orientation between a bone stabilization implant such as a bone plate and an aiming device for anchoring the implant to an internal part of a body.

The invention further relates to a method for detachably establishing a spatial orientation between a body implant and an aiming device, in particular between a bone stabilization implant and an aiming device for anchoring the implant to an internal part of a body.

In order to allow for a reliable stabilization of a broken bone in its normal position, special bone stabilizing implants are frequently used. Such implants are for instance metal plates, which are made e.g. from surgical steel. Plates used for such purposes are usually fixed to the bone parts by means of threaded screws, which are driven into the bone tissue after so-called pre-drilled or pilot-drilled holes have been generated within the bone tissue. These pre-drilled holes allow for a reliable screwing procedure whereby the risk of further destroying the bone with the screw is significantly reduced.

In order to facilitate the drilling of these pre-drilled holes there are known so-called aiming devices or aiming blocks, which work like a drilling jig. Thereby, an aiming device is detachably fixed to the metal plate in a spatial precise position.

Aiming devices are also used in connection with locking nails, which are driven into intramedullary canal of the bone. Thereby, the position of a cross bore within the interlocking nail can be determined precisely. The cross bore is adapted to accommodate a fixing screw, which is driven crosswise through the corresponding bone section.

U.S. Pat. No. 6,224,601 B1 discloses the use of an aiming device in an osteosynthesis auxiliary for the treatment of subtrochanteric, peritrochanteric and femoral-neck fractures.

There may be a need for a medical system, medical system parts and a method for spatially adjusting an aiming device relative to a body implant, which allow for an easy, quick and precise relative positioning of an aiming device with respect to a body implant.

SUMMARY OF THE INVENTION

In order to fulfill the need defined above there are provided a body implant, an adaptor device, a medical system and a method for detachably establishing a spatial orientation between a body implant and an aiming device.

According to an aspect of the invention there is provided a body implant, in particular a bone stabilizing implant. The body implant comprises (a) through holes for anchoring the implant to an internal part of a body by means of fastening elements and (b) a contour portion, which is designed in such a manner that an adaptor device for establishing a spatial orientation between the body implant and an aiming device can be detachably fastened to the body implant by means of a mechanical form-fit connection. The contour portion comprises a central opening and a groove. Thereby, the central opening might interact with the adaptor device like a mortise and a tenon such that the relative position between the implant and the adaptor device is defined precisely. The central opening preferably has a circular respectively a cylindrical shape such that during manufacturing of the body implant the opening can easily be formed within the implant by means of a simple drilling procedure.

The groove may be formed in such a manner that it might mutually interact with a corresponding protrusion from the adaptor device. This interaction may be similar to the well-known mechanical interaction between tongue and groove. Thereby, also a rotational movement of the adaptor device with respect to the body implant is effectively prevented.

This aspect of the present invention is based on the idea that a form-fit connection between the body implant and the adaptor device can be realized if the adaptor device and the corresponding contour portion formed at the body implant spatially interact with each other in such a manner that these parts mutually intervene and/or engage with each other. Thereby, a precise relative spatial orientation of the body implant and the adaptor device can be maintained.

The body implant may be a plate for stabilizing a broken bone in its normal position. The plate may be used for stabilizing the proximal tibia. Typically, the fastening elements are screws, which can be driven into different portions of a broken bone.

The aiming device has a structure, which is related to at least some of the through holes formed within the body implant. Such a structure typically represents a drilling jig in order to allow for an easy and for a precise pre-drilling of holes within the broken bone. This pre-drilling is carried out through the through holes formed in the body implant such that it is guaranteed that the pre-drilled holes spatially correspond to the through holes of the body implant.

During an operation of a patient it has to also be ensured that the adaptor device and the aiming device are rigidly fixed to each other. Therefore, the form locked adaptor device provides a mechanically stable platform for the aiming device.

According to an embodiment of the present invention the central opening is a through hole. This provides the advantage that the central opening may be formed by means of an in particular simple drilling procedure, because it is not necessary to take care of the actual drilling depth during the drilling procedure.

According to a further embodiment of the present invention the contour portion comprises at least one further groove. This may provide the advantage that the relative spatial position between the adaptor device and the body implant can be established even more precisely and in a more reliably way.

In this respect it is clear that the adaptor device has to be formed in a complementary shape with respect to the contour portion. Thereby, a form-fit is possible not only with respect to the central opening and to one groove but with respect to the central opening and to the at least two grooves.

According to a further embodiment of the present invention the first groove and the second groove are arranged in an asymmetric manner with respect to the central opening. This may provide the advantage that the adaptor device and the body implant can be mechanically connected to each other only in a predefined relative orientation. Therefore, an accidentally wrong assembling of these parts can be effectively prevented.

According to a further embodiment of the present invention the contour portion comprises a locking element which is designed in such a manner that the adaptor device is lockable to the body implant by means of a locking mechanism assigned to the adaptor device.

The provision of a locking element has the advantage that an unintentional opening of the mechanical form-fit connection between the adaptor device and the body implant may be prevented effectively. Of course, the adaptor device may be removed from the implant by an appropriate procedure after a surgery procedure has been successfully carried out. Thereby, the surgery procedure may benefit from using the aiming device.

Preferably, in addition to the form-fit connection between the adaptor device and the body implant the locking element causes also a force-fit connection between the body implant and the adaptor device by pressing these parts against each other. Thereby, the mechanical connection between the implant and the adaptor device may be improved with respect to the spatially precision and/or with respect to the mechanical stability under load.

The locking element may be an edge or any other kind of projection, which is suitable to be engaged with a locking device.

According to a further embodiment of the present invention the locking element is an internal screw thread. This has the advantage that the locking mechanism of the adaptor device might be realized by means of a simple screw. Thereby, a stable mechanical connection between the adaptor device and the implant may be achieved by pressing these parts mutually against each other. Thereby, both a form-fit and a force-fit connection between the adaptor device and the implant may be realized.

According to a further aspect of the invention there is provided an adaptor device for detachably establishing a spatial orientation between a body implant and an aiming device, in particular between a bone stabilization implant and an aiming device for anchoring the implant to an internal part of a body. The adaptor device comprises (a) an end portion, which is adapted to be detachably fastened to a contour portion of the body implant by means of a mechanic form-fit connection, and (b) a coupling portion, which is adapted to be mechanically connected to the aiming device.

Also this aspect of the present invention is based on the idea that a precise form-fit connection between the body implant and the adaptor device can be realized if the adaptor device and the corresponding contour portion formed at the body implant spatially interact with each other in such a manner that these parts mutually intervene and/or engage with each other. Thereby, a precise relative spatial orientation of the body implant and the adaptor device can be maintained.

The adaptor device comprises at least at one side a three-dimensional surface profile, which is formed in such a manner that it corresponds in a complementary manner to the contour portion of the body implant. Thereby, the adaptor device and the body implant mutually engage with each other.

The adaptor device may be formed integrally from a single material or a material composition. However, the adaptor device may alternatively be assembled from different elements.

According to an embodiment of the present invention the end portion is assigned to a dowel pin, which is designed in such a manner that the dowel pin can be detachably fastened to a central opening of the contour portion. Thereby, the central opening might interact with the adaptor device like a mortise and a tenon such that a relative position between the body implant and the adaptor device is defined in a spatially precise manner. The central opening preferably has a circular respectively a cylindrical shape such that the opening can easily be formed within the implant.

Preferably, the dowel pin may be fastened to the body implant by inserting one end of the dowel pin into the central opening.

According to a further embodiment of the present invention the dowel pin comprises a locking mechanism which is designed in such a manner that the adaptor device is lockable to the body implant by means of a locking element assigned to the body implant.

The provision of a locking mechanism has the advantage that an unintentional opening of the mechanical connection between the adaptor device and the body implant may be effectively prevented. Of course, the adaptor device may be removed from the implant by an appropriate procedure after a surgery procedure using the aiming device has been successfully completed.

In order to provide for a stable connection between the body implant, in particular the contour portion, and the adaptor element, in particular the dowel pin, the contour portion may comprise an edge or any other kind of projection, which is suitable to be engaged with the locking mechanism.

According to a further embodiment of the present invention the locking mechanism comprises an external screw thread. Preferably, the dowel pin might comprise an external screw thread at least at one end portion of the dowel pin. This has the advantage that a mechanically stable connection between the body implant and the adaptor device might be realized by simply screwing the dowel pin into a threaded central opening of the contour portion. Thereby, a stable mechanical connection between the adaptor device and the implant may be achieved by means of a very simple and effective fastening procedure.

According to a further embodiment of the present invention a coupling portion is assigned to a handling device comprising a through hole such that the handling device is slideable over the dowel pin. This may provide the advantage that the adaptor device can be easily attached to the implant whereby an appropriate relative orientation between the adaptor device and the implant is automatically ensured.

According to a further embodiment of the present invention the handling device comprises a handle. The handle may protrude laterally from the central part of the handling device which central part is equipped with the through hole. This may provide the advantage that during an operation a manual handling of both the adaptor device and the body implant detachably fastened to the adaptor device is facilitated. Preferably, the handle comprises an ergonomic handhold.

According to a further embodiment of the present invention the handling device comprises a protrusion. The protrusion is formed in such a way that the adaptor device is capable of engaging into a groove of the contour portion of the body implant. The protrusion is formed in such a manner that it might interact with a corresponding groove formed within the body implant. This interaction may be similar to the well-known mechanical interaction between a tongue and groove. Thereby, also a rotational movement of the adaptor device with respect to the body implant may effectively be prevented.

According to a further embodiment of the present invention the handling device comprises at least one further protrusion. This may provide the advantage that the relative spatial position between the adaptor device and the body implant can be established even more precisely and in a more reliably way.

In this respect it is clear that the contour portion of the body implant has to be formed in a complementary shape with respect to the relevant surface of the handling device such that the adaptor device form-fits to the central opening and to the at least two grooves.

According to a further embodiment of the present invention the first protrusion and the second protrusion are arranged in an asymmetric manner with respect to the central opening. This may provide the advantage that adaptor device and the body implant can be mechanically connected to each other only in a predefined relative angular orientation. Therefore, an accidentally wrong assembling may be prevented.

According to a further embodiment of the present invention the adaptor device further comprises a clamping element, which is adapted for being mounted onto the dowel pin in order to maintain the handling device in a position wherein the handling device abuts against the body implant.

In case the handling device comprises one or more protrusions, which engage into corresponding grooves formed within the body implant, the clamping element is capable of reliably securing the handling device and the implant in a spatially stable relative position with respect to each other.

According to a further embodiment of the present invention the clamping element is a nut. Preferably, the clamping element is a cap nut such that the upper portion of the dowel pin is protected and the adaptor device exhibits no sharp edges or corners.

The nut may be provided with an internal screw thread. Provided that the dowel pin is equipped with a corresponding external screw thread this allows for both an easy and a secure fastening of the handling device to the body implant.

According to a further embodiment of the present invention the handling device is designed in such a manner that the aiming device is detachably attachable to the handling device. This may provide the advantage that a predefined relative spatial position between the aiming device and the body implant may be established precisely.

This is particularly helpful if the implant is a plate, which is used for bone stabilization. Such a plate may be used in order to fix a broken bone in its anatomically correct position. Thereby, the plate is attached to different parts of the bone by means of screws, pins, loops, et cetera. In particular when screws are used for attaching the plate, an aiming device may be very helpful, which aiming device comprises a drilling jig. Thereby, an operator, and in particular a surgeon, is capable of precisely drilling holes into the bone, whereby each hole is formed exactly at the proper position with respect to a corresponding through hole formed in the plate.

According to a further aspect of the invention there is provided a medical system for detachably establishing a spatial orientation between a body implant and an aiming device, in particular between a bone stabilization implant and an aiming device for anchoring the implant to an internal part of a body. The medical system comprises a body implant according to an aspect or an embodiment described above. The medical system further comprises an adaptor device according to an aspect or an embodiment described above.

According to a further aspect of the invention there is provided a method for detachably establishing a spatial orientation between a body implant and an aiming device, in particular between a bone stabilization implant and an aiming device for anchoring the implant to an internal part of a body. The described method comprises (a) fastening a dowel element to a contour portion of the body implant, (b) fixing a handling device to the dowel element such that the handling device abuts against the body implant in a form-fit manner, (c) mounting a clamping element onto the dowel element in order to secure the relative spatial position between the handling device and the body implant, and (d) attaching the aiming device to the handling device.

This aspect of the invention is based on the idea that a mechanically stable spatial relative position between the body implant and the aiming device can be established by means of a multi-step process. First, there is established a precise spatial position between the handling device and the body implant by fixing the handling device to the dowel element fastened to the contour portion of the body implant. Second, there is established a precise spatial position between the handling device and the aiming device by attaching the aiming device to the handling device in an appropriate spatial orientation.

According to an embodiment of the invention the step of fastening a dowel element to a contour portion of the body implant comprises inserting a dowel pin into a central opening of the contour portion. Using a dowel pin as the dowel element may provide the advantage that the dowel pin can be used both (a) as a centering element in order to provide for an easy assembling of the adaptor device and (b) as a mechanical fastener in order to provide for a stable and reliable mechanical connection between the handling device and the body implant.

According to a further embodiment of the present invention the step of inserting a dowel pin into a central opening of the contour portion comprises screwing the dowel pin into an internal screw thread, which is provided in the central opening. As has already been mentioned above, this has the advantage that the locking mechanism of the adaptor device might be realized by means of a simple screw thread. Thereby, a stable mechanical connection between the adaptor device and the body implant may be achieved.

According to a further embodiment of the invention the step of fixing a handling device to the dowel element comprises (a) using a handling device comprising a through hole and (b) sliding the handling device over the dowel pin. This may provide the advantage that an easy and mechanical stable connection between the handling device and the body implant can be established.

According to a further embodiment of the present invention the step of sliding the handling device over the dowel pin comprises rotating the handling device around the dowel pin such that a protrusion, which is provided at the handling device, engages into a groove which is provided at the contour portion.

Preferably, the rotating movement is a bidirectional swivel movement, which is accomplished in the course of the sliding movement in particular when the sliding movement has already come to an end. The described rotational movement may provide the advantage that an engagement between complementary three-dimensional surface portions of the body implant and the handling device, respectively, may be achieved by means of a simple manual movement of the handling device with respect to the body implant.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless otherwise notified, in addition to any combination of features belonging to one subject matter also any combination between features relating to different subject matters, in particular between features of the apparatus type claims and features of the method type claims is disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

BRIEF DESCRIPTION OF THE DRAWINGS

FIG. 1a shows a bone stabilizing plate representing a body implant according to an embodiment of the invention;

FIG. 1b shows the upper part of the plate depicted in FIG. 1a;

It is noted that in different figures, similar or identical elements are provided with the same reference signs or with reference signs, which are different from the corresponding reference signs only within the first digit.

DETAILED DESCRIPTION

Figures 1A, 1B:
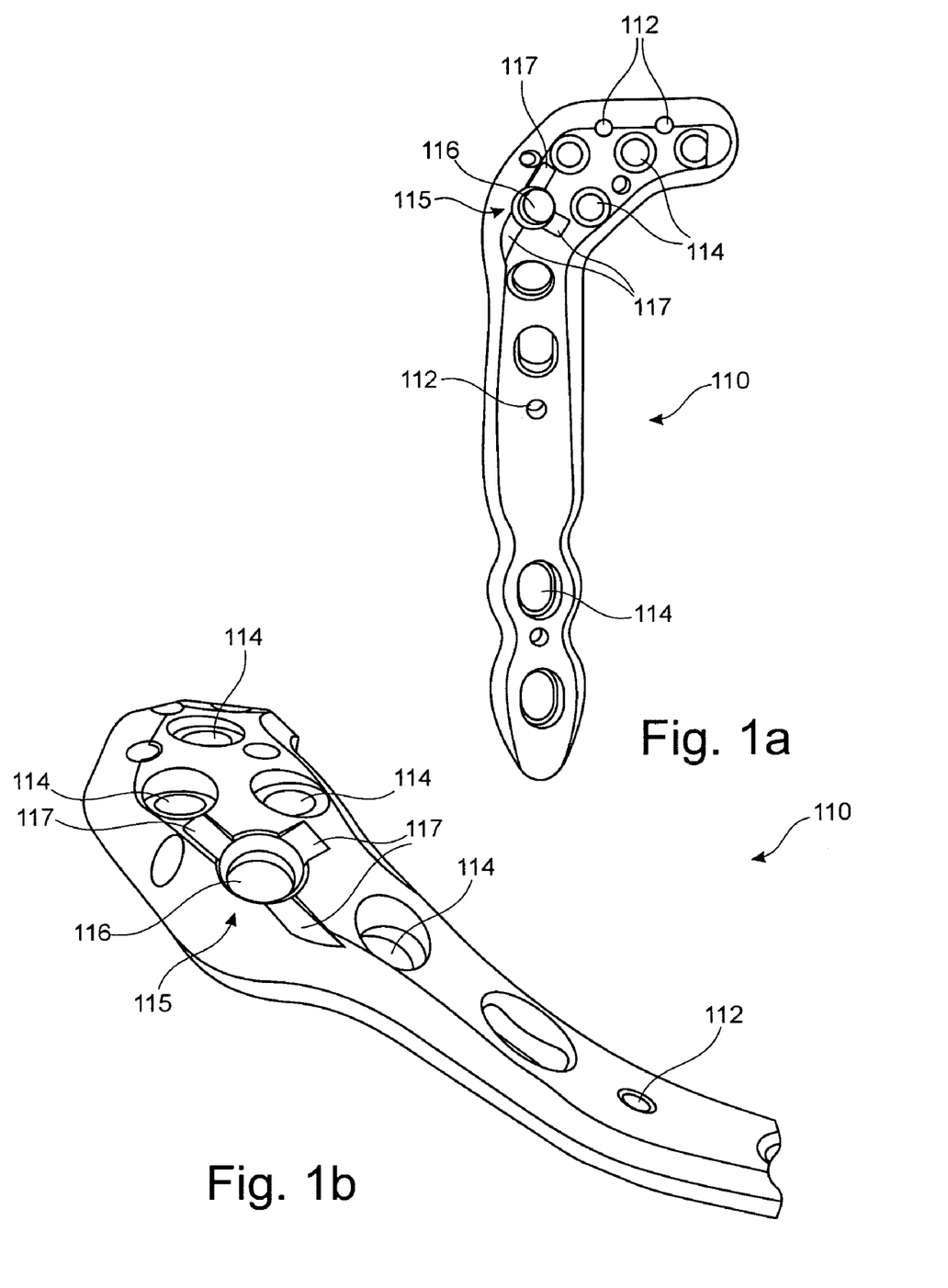

Referring to FIG. 1a and FIG. 1b there is shown a preferred bone stabilizing plate 110 in the form of a body implant such as a plate 110 according to a preferred embodiment of the invention. FIG. 1b depicts a slightly enlarged view of the upper part of plate 110.

The bone stabilizing plate 110 comprises a plurality of through holes 114. The through holes 114 may be used for inserting screws (not depicted) for fixing plate 110 to a bone or to a bone fragment such that all parts of the bone are attached to the bone stabilizing plate 110.

Plate 110 further comprises a contour portion 115, which is a three-dimensional profiled surface portion of an upper surface of the plate 110. The contour portion 115 comprises a preferably centrally located opening 116 and three grooves 117, which extend out radially from the central opening 116.

As can be seen from FIG. 1c which depicts a cross sectional view of the central opening 116 formed with plate 110, the internal side walls of the central opening 116 are, in the preferred embodiment, provided with an internal screw thread 118.

Figure 2:
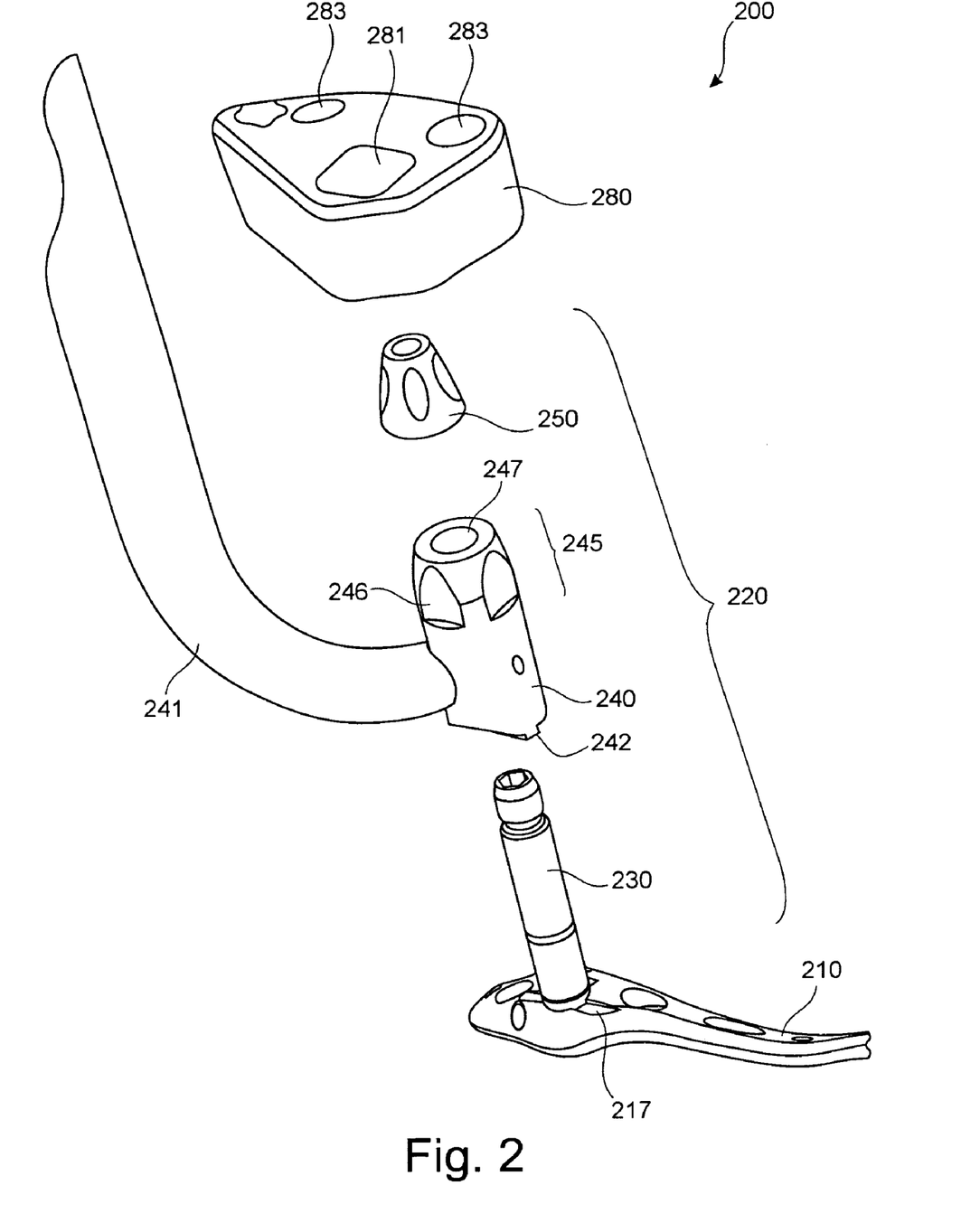
FIG. 2 shows an exploded view of a medical system comprising the plate depicted in FIG. 1a and an adaptor device for holding an aiming device in a spatially precise orientation with respect to the plate.

FIG. 2 shows an exploded view of a medical system 200 comprising the plate 210 depicted in FIG. 1a and an adaptor device 220 for holding an aiming device 280 in a spatially precise orientation with respect to the plate 210. The adaptor device 220 comprises several parts, a dowel pin 230, a handling device 240 and a clamping element 250.

In the preferred embodiment the dowel pin 230 has the shape of an elongated shaft. A lower end of the shaft or pin 230 is provided with an external screw thread such the shaft or pin 230 can be screwed into the central opening 116 of plate 210, which central opening is provided with an internal screw thread 118.

The handling device 240 comprises a through hole 247 such that the dowel pin 230 might be inserted into handling device 240. In other words, handling device 240 might be pinned onto dowel pin 230.

The handling device 240 further comprises a handle 241, which preferably is formed in such a manner that handle 241 represents an ergonomic handhold. This provides the advantage that during an operation a manual handling of the whole medical system 200 is facilitated.

In order to provide for a stable mechanical connection between handling device 240 and plate 210 a lower surface of the handling device 240 is formed in such a manner that a three-dimensional profiled surface is provided, which corresponds in a complementary way to the contour portion 115 of the plate 210. According to the embodiment described here the three-dimensional profiled contour comprises three protrusions 242, which respectively engage within a corresponding groove 217 formed within the body implant 210. An engagement of the protrusions 242 with the corresponding grooves 217 has the effect, that a rotational movement of the handling device 240 with respect to the dowel pin 230 is effectively prevented.

According to the embodiment described here, the grooves 117/217, which might also be classified as positioning slots, have a maximum depth of approximately 0.7 mm. However, also other dimensions for the grooves 117 may be applicable.

In the preferred embodiment the protrusions 242 and consequently also grooves 217 are arranged in an asymmetric manner around the central opening respectively the through hole 247. This has the effect that handling device 240 and body implant 210 can be mechanically connected to each other only in a predefined relative angular orientation. Therefore, an accidentally incorrect assembling of these parts is automatically prevented.

It should be noted that protrusions 242 corresponding to grooves 117/217 protrude from the through hole 247 and grooves 217 extend respectively from the central opening 116 in such a manner that when a typical bending load is exerted between the plate 210 and the handling device 240 the dowel pin 230 is subjected to a tensile stress only. Thereby, the stability of the whole adaptor device is improved.

Handling device 240 furthermore comprises a coupling portion 245, which is formed at an upper section of handling device 240. The coupling portion 245 is represented by a special shape of the outer surface 246 of handling device 240. This outer surface 246 is formed in such a manner that it complementary fits to an inner surface (not depicted) of an opening 281 formed within an aiming device 280. Thereby, the aiming device may be detachably fastened to handling device 240 by pushing aiming device 280 into the proper position on the coupling portion 245 of handling device 240. In order to provide for a secure but detachable connection the aiming device 280 is connected to handle device 240 by means of a so-called quick coupling device which are well known to those skilled in the art.

In order to prevent aiming device 280 from being assembled to the coupling portion 245 in the wrong position the outer surface 246 of handling device 240 are distributed in a rotational asymmetric manner.

Clamping element 250 is adapted to be mounted onto dowel pin 230 in order to maintain handling device 240 in a position wherein handling device 240 abuts against body implant 210. Since handling device 240 comprises three protrusions 242, which engage into corresponding grooves 217, clamping element 250 is capable of reliably securing handling device 240 and plate 210 in a spatially stable relative position with respect to each other.

As can be seen from FIG. 2, the clamping element is a cap nut such that the upper portion of dowel pin 230 may be covered. This has the advantage that in an assembled state no edges of dowel pin 230 project or protrude above the upper surface of aiming device 280.

Preferably, dowel pin 230 is provided with a spring ring (not depicted). The spring ring is adapted to engage into a corresponding snap ring groove (not depicted), which is provided at the inner side wall of the through hole 247 formed within handling device 240. This has the advantage that during an assembling procedure of the adaptor device 220 handling device 240 is temporarily fixed to the dowel pin 230 by means of a snapping mechanism prior to the cap nut 250 being completely screwed onto the external screw thread of dowel pin 230. Thereby, the assembling procedure of the adaptor device 220 may be facilitated significantly.

Targeting or aiming device 280 represents a drilling jig comprising an opening 281 for connection with the coupling portion of handling device 240. The aiming device 280 further comprises several through holes 283 for a precise and easy pre-drilling of holes into a bone fragment, which is located directly beneath the bone stabilizing plate 210. Thereby, the through holes 283 represent a drilling jig allowing for a minimal invasive and percutaneous surgery technique. When the aiming device 280 is properly mounted to the handling device 240 the holes 283 of the aiming device 280 are aligned with the holes 214 in the plate 210.

FIGS. 3a to 3g illustrate a procedure for assembling the medical system 200 depicted in FIG. 2.

Figure 3A:
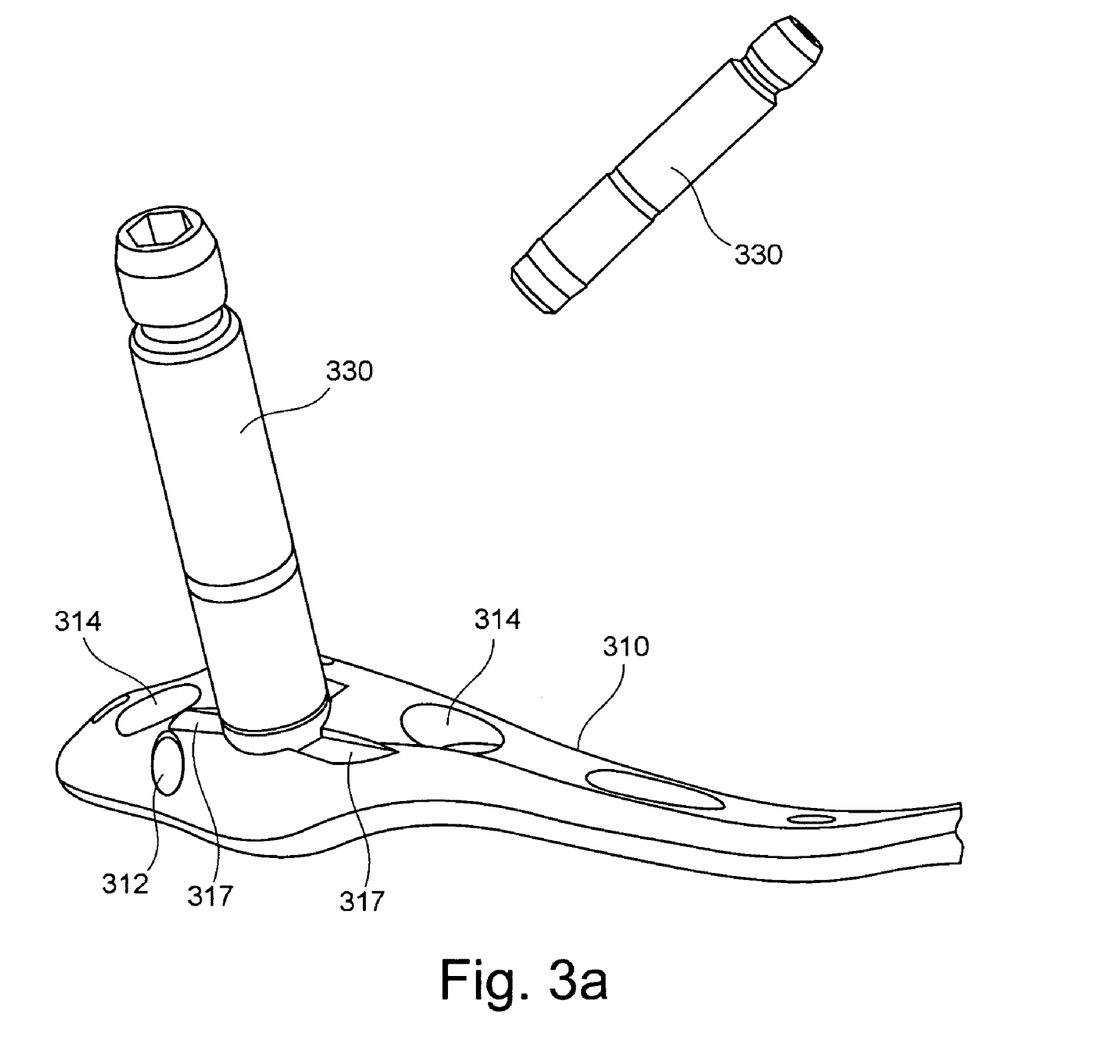
FIGS. 3a to 3d illustrate a procedure for assembling the medical system depicted in FIG. 2.

As can be seen from FIG. 3a the assembling starts with inserting the dowel pin 330 into the central opening 116 (see FIG. 1) of the bone stabilizing plate 310, which comprises several through holes 314. The relevance of the through holes 314 has already been explained above.

In order to provide for both a spatially stable and a mechanically reliable connection between the plate 310 and the dowel pin 330, the outer surface at the lower portion of the dowel pin 330 is provided with an external screw thread 331. This thread corresponds to an internal screw thread 118 provided at the inner side wall of central opening 116 (see FIG. 1). Therefore, dowel pin 330 is fastened to plate 310 by screwing dowel pin 330 into central opening 116. In order to facilitate the screwing the upper portion of dowel pin 330 is provided with a drive socket 333.

Figure 3B:
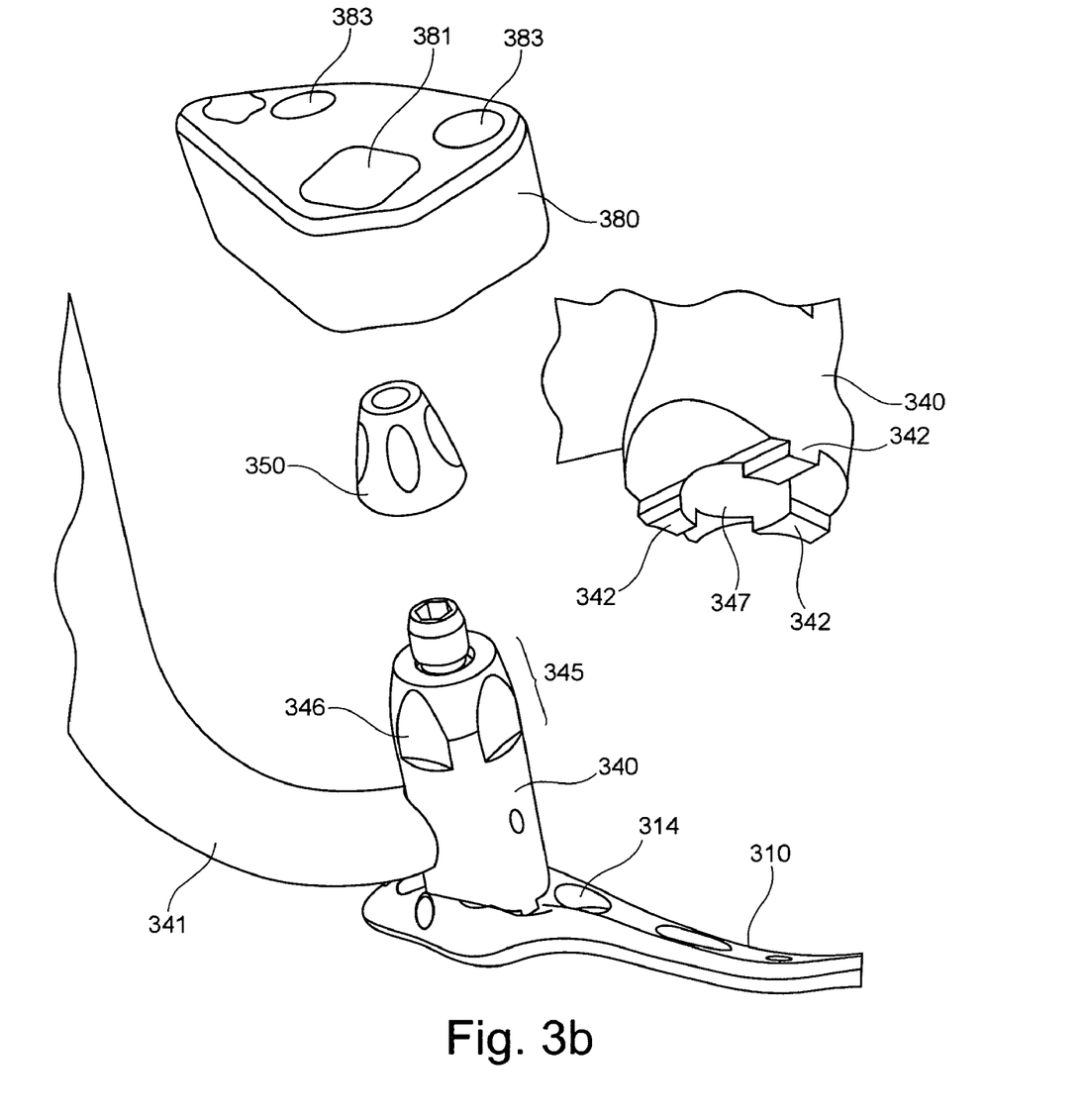

Dowel pin 330 is depicted individually in FIG. 3b. As has already been described above dowel pin 330 has the shape of an elongated shaft. A lower end of the shaft 330 is provided with an external screw thread 331 such that shaft 330 can be screwed into the central opening 116 of plate 310, which central opening is provided with an internal screw thread 118. Also an upper end of the shaft 330 is provided with an external screw thread 332 such that cap nut 250 depicted in FIG. 2 can be screwed onto the dowel pin 330.

According to the preferred embodiment described herein dowel pin 330 is a hollow shaft having an outer diameter of approximately 6.0 mm and an inner diameter of approximately 2.6 mm. However, also other dimensions for dowel pin 330 may be applicable.

Figure 3C:
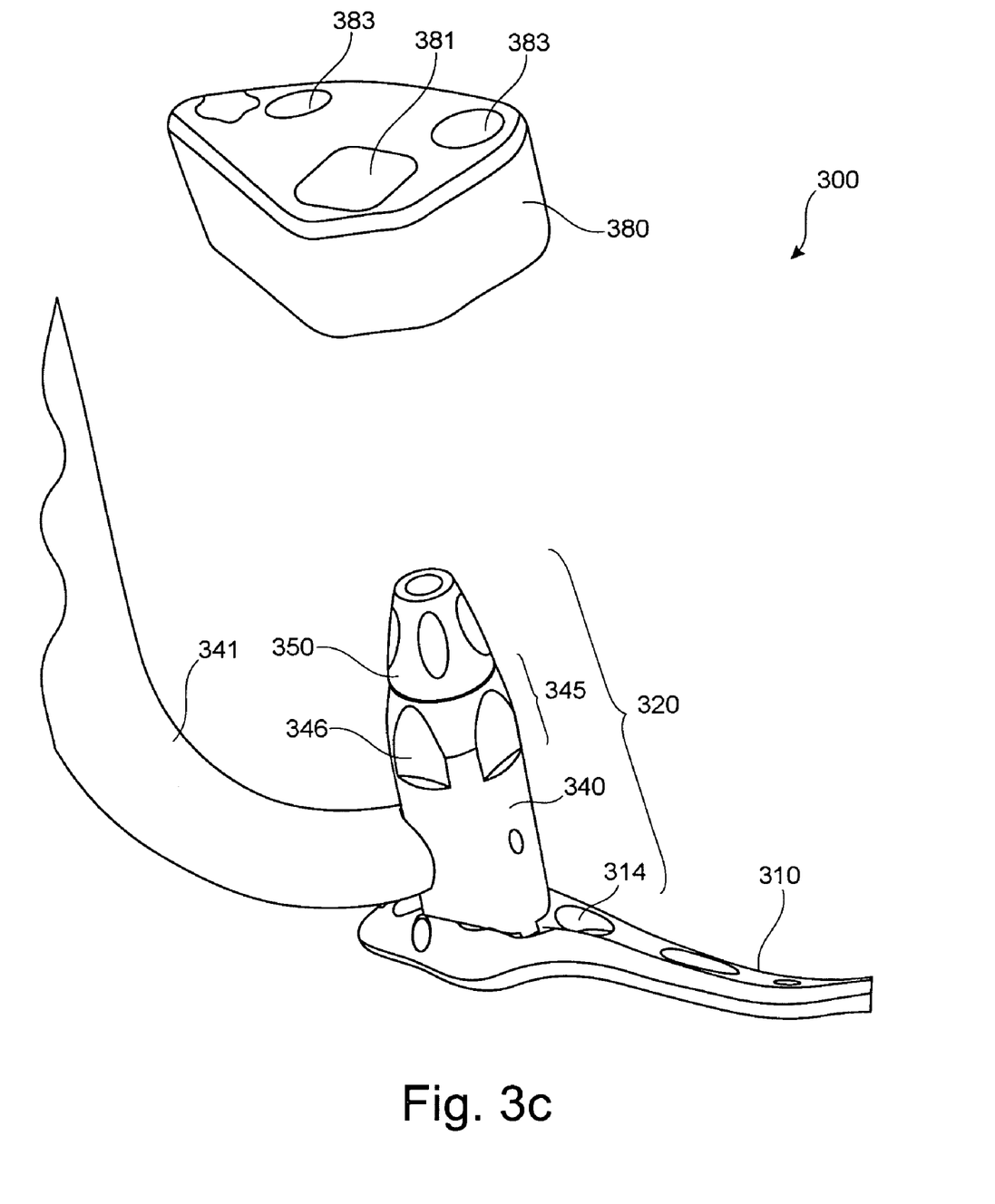

FIG. 3c shows the medical system in an advanced assembled state. A handling device 340 is pinned on dowel pin 330. As can be seen from the small inset in FIG. 3b, which depicts the lower surface of handling device 340, the handling device 340 comprises an opening 347 for receiving dowel pin 330 and three protrusions 342 for being engaged into the grooves 317 of the plate 310.

When being assembled, handling device 340 abuts against the contoured portion of the plate 310 such that the protrusions 342 engage into the grooves 317. In order to quickly find the correct relative angular position between the protrusions 342 of handling device 340 and grooves 317 of the plate 310, the handling device 340 is rotated around the dowel pin when handling device 340 is pushed over dowel pin 330. The handling of the handling device 340 is facilitated by the handle 341, which is formed at the handling device 340.

Figure 3D:
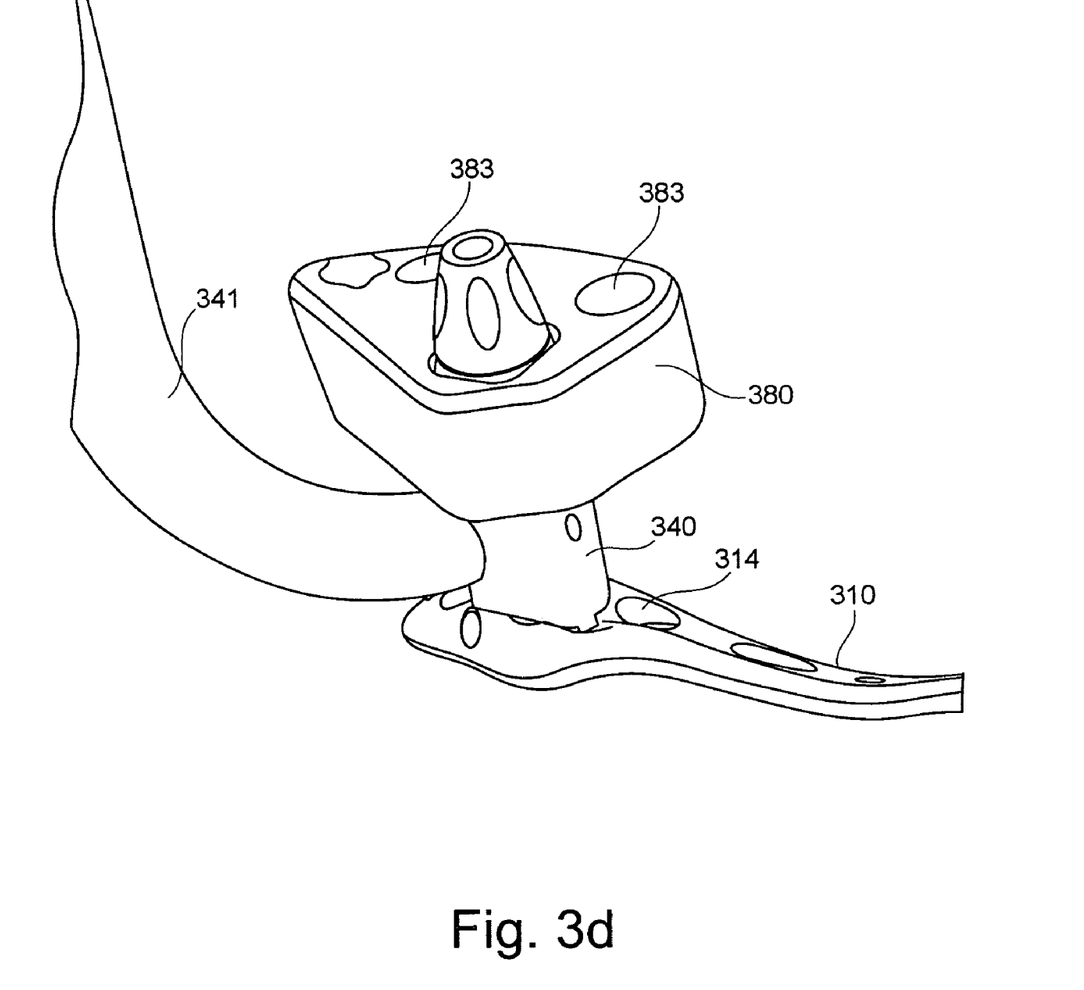

FIG. 3d shows an enlarged view of the lower surface of the handling device 340. This surface is provided with three protrusions 342, which project from the lower surface. In order to prevent that the handling device 340 is attached to the plate 310 in a wrong angular position the protrusions 342 are arranged in an asymmetric T-form.

FIG. 3e shows a cross sectional view of the cap nut 350. In order to allow for a reliable and stable connection between plate 310 and handling device 340 cap nut 350 is provided with an internal screw thread 351. Dowel pin 330 is equipped with a corresponding external screw thread 332 which allows for both an easy and a secure fastening of handling device 340 to body implant 310.

FIG. 3f shows the medical system 300 in a further advanced assembled state. A clamping element 350 is fastened to the upper portion of dowel pin 330. The preferred clamping element is a nut having an internal screw thread 351 that fits to a corresponding external screw thread 332 provided at the outer surface of the upper section of dowel pin 330. Therefore, by screwing nut 350 onto dowel pin 330 handling device 340 is pressed against plate 310. Thereby, also a force-fit connection between the handling device 340 and the plate 310 is provided such the relative spatial position between these two parts 340 and 310 being precisely defined by protrusions 342 and the corresponding grooves 317 can be maintained even under a mechanical load.

In this respect it is pointed out that the protrusions 342 and the corresponding grooves 317 are designed to cause a form-fit connection between the handling device 340 and the plate 310 whereas the nut 350 being threaded screwed onto the dowel pin 330 and the dowel pin 330 being screwed into the plate 310 causes a force-fit connection between the handling device 340 and the plate 310.

In order to provide a basis for an aiming device 380, the handling device 340 comprises a coupling portion 345. An outer surface 346 is formed in such a manner that it complementary fits to an inner surface (not depicted) of an opening 381 formed within aiming device 380. Thereby, the aiming device may be detachably fastened to the handling device 340 by pushing the aiming device 280 into the proper position on coupling portion 345.

In the assembled state dowel pin 330, handling device 340 and clamping element 350 represent an adaptor device 320, which allows for a precise and stable positioning of aiming device 380 with respect to plate 310.

FIG. 3g shows the medical system 300 in the final assembled state. The aiming device 380 is pushed into the proper position onto coupling portion 345. In order to provide for a precise and easy pre-drilling of holes into a bone fragment, which is located directly beneath the bone stabilizing plate 310, aiming device 380 is provided with an opening 381 and several through holes 383. The spatial arrangement of through holes 383 represents a drilling jig. Therefore, the aiming device helps a surgeon for pre-drilling holes into a broken bone exactly at positions, which correspond to the through holes 314 of the plate 310.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

In order to recapitulate the above described embodiments of the present invention one can state: There is described a medical system 200, system parts 210, 220 and a method for detachably establishing a spatial orientation between a body implant 210 and an aiming device 280. Thereby, a contoured portion 115 of a body implant 110, 210 is designed in such a manner that an adaptor device 220 can be detachably fastened to the body implant 110, 210 by means of a mechanic form-fit connection. The adaptor device 220 provides a basis for an aiming device 280 such that the aiming device 280 may be detachably positioned in a stable spatial position with respect to the body implant 210. Preferably, the adaptor device 220 comprises different elements like a dowel pin 230, a handling device 240 and a clamping element 250, which elements allow for a quick and easy assembling and disassembling of the adaptor device 220.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantation system for a bone stabilizing implant comprising:
   a bone stabilizing implant having a body portion with a plurality of through holes for anchoring the implant to part of a bone by means of fastening elements and a contour portion having a central opening therein, wherein the central opening is a through hole, and at least one groove having a bottom surface;
   an aiming device for detachable attachment to the implant; and
   an adaptor for establishing a spatial orientation between the implant and the aiming device, the adaptor having a form-fit connector at one end thereof for engaging a first groove of the at least one groove on the counter portion, wherein the form-fit connector includes a first protrusion corresponding in shape to the groove for engaging the bottom surface of the first groove; wherein the contour portion comprises a second and a third groove each spaced and angularly offset from the first groove and each having a bottom surface, wherein the first, second and third grooves are arranged in an asymmetric manner with respect to the central opening with at least one angle of an angle between the first and second grooves, an angle between the first and third grooves and an angle between the second and third grooves being unequal to the other two angles, and said adaptor form-fit connector has two further protrusions each for engaging a groove bottom surface of the second and third grooves, so that the aiming device and the implant can be mechanically connected to each other only in one predefined relative angular orientation.

2. The system according to claim 1, wherein the contour portion comprises a locking element for engaging a locking mechanism carried by the adaptor device for locking the implant to the adaptor.

3. The system according to claim 2, wherein the locking element is an internal screw thread.

4. An adaptor device for detachably establishing a spatial orientation between an implant and an aiming device for anchoring the implant to an internal part of a body, the adaptor device comprising:
   a dowel pin, which is designed in such a manner that the dowel pin can be detachably fastened to an opening in a contour portion of the implant;
   an end portion for detachably coupling the implant by the engagement of mating form fitting elements formed on the adaptor end portion and on the contour portion of the implant, wherein the mating form-fitting elements are three protrusions and three grooves each groove having a shape matching a shape of one of the protrusions formed on the contour portion, wherein the protrusions and the grooves are angularly offset and are arranged in an asymmetric manner with respect to the opening with at least one angle of an angle between a first and a second groove, an angle between the first and a third groove and an angle between the second and third grooves being unequal to the other two angles;
   a coupling portion, adapted to be mechanically connected to the aiming device, wherein the coupling portion includes a handling device, which handling device comprises a through hole such that the handling device is slideable over an outer surface of the dowel pin.

5. The adaptor device according to claim 4, wherein the dowel pin comprises a locking mechanism which is lockable to the body implant by means of a locking element on the implant.

6. The adaptor device according to claim 5, where the locking mechanism comprises an external screw thread.

7. The adaptor device according to claim 4, wherein the handling device comprises a handle.

8. The adaptor device according to claim 4, further comprising a clamping element, which is adapted for mounting onto the dowel pin in order to engage and maintain the handling device in a position wherein the at least one handling device protrusion abuts against the implant.

9. The adaptor device according to claim 8, wherein the clamping element is a nut.

10. The adaptor device according to claim 4, wherein the aiming device is detachably attachable to the handling device.

11. A method for detachably establishing a spatial orientation between a bone implant and an aiming device for anchoring the implant to a bone, the method comprising:
   fastening a dowel element to a contour portion of the body implant, the contour portion having form-fitting elements in an outer surface thereof, wherein the form-fitting elements are three grooves in the outer surface of the implant, wherein the grooves are arranged offset with at least one angle of an angle between a first and a second groove, an angle between the first and a third groove and an angle between the second and third grooves being unequal to the other two angles and spaced from each other;
   fixing a handling device having an aiming device to the dowel element such that the handling device has mating form-fitting elements which abuts against the form-fitting elements of the implant contour portion, wherein the mating form-fitting element's are protrusions having a shape corresponding in shape to the grooves, wherein fixing the handling device to the dowel element comprises using a handling device comprising a through hole and sliding the handling device over an outer surface of the dowel pin;
   mounting a clamping element onto the dowel element in order to secure the relative spatial position between the handling device and the body implant by the engagement of the form-fitting elements on the dowel element and the contour portion; and using the aiming device to attach the implant to bone.

12. The method according to claim 11, wherein the fastening of the dowel element to the contour portion of the body implant comprises inserting a dowel pin into an opening in the contour portion.

13. The method according to claim 12, wherein inserting a dowel pin into the opening of the contour portion comprises screwing the dowel pin into an internal screw thread which is provided in the opening.

14. The method according to claim 11, wherein sliding the handling device over the dowel pin comprises rotating the handling device around the dowel pin such that the form-fitting elements, which are provided at an end of the handling device, engages into the form-fitting elements provided in the contour portion, wherein the form-fitting elements on the handling device are the protrusions and the form-fitting elements on the contour portion are the grooves.

15. A bone plate implantation system comprising:

a bone plate having a plurality of through bores extending from a bone contacting surface to an outer surface thereof including an alignment opening having a plurality of grooves extending outwardly therefrom along said outer surface of said bone plate;

a dowel shaft element having a first end for engaging said alignment opening having the grooves extending therefrom and a second end spaced from said first end along an axis;

an adaptor having a bore for receiving said dowel shaft and a first end having a plurality of protrusions for insertion into said plurality of grooves on said plate outer surface the protrusions corresponding in shape to the grooves, wherein the grooves are arranged asymmetrically around said bore in said bone plate and are spaced from and angularly offset from each other with an angle between a first of the plurality of grooves and a second of the plurality of grooves are unequal in opposite directions around a circumference of the said bore; and a targeting device mountable on a second end of said adaptor axially spaced from the outer surface of the bone plate, the targeting device having a drill guide bore.

16. The implantation system of claim 15, wherein a clamping element is moveably mounted on the second end of the dowel shaft element for engaging the second end of said adaptor for clamping said adaptor to said plate and clamping said protrusions against a bottom surface of said grooves.

17. The implantation system as set forth in claim 16 wherein each protrusion has two spaced side walls and each groove has two spaced side walls, which groove side walls extend outwardly from the bottom surface of each groove and contact the sidewalls of each protrusion on clamping to prevent relative rotation between the plate and the adaptor.

18. The implantation system as set forth in claim 15 wherein said second end of said adaptor includes surfaces for aligning the targeting device drill guide bore with one of the plurality of through bores in the bone plate.

* * * * *